(12) United States Patent
Karimi et al.

(10) Patent No.: US 12,010,206 B2
(45) Date of Patent: Jun. 11, 2024

(54) SYSTEM FOR ENCODING GENOMICS DATA FOR SECURE STORAGE AND PROCESSING

(71) Applicant: Elimu Informatics, Inc., El Cerrito, CA (US)

(72) Inventors: Seemeen S. Karimi, La Jolla, CA (US); Aziz A. Boxwala, La Jolla, CA (US); Robert Harold Dolin, Gold Hill, OR (US)

(73) Assignee: ELIMU INFORMATICS, INC., El Cerrito, CA (US)

( * ) Notice: Subject to any disclaimer, the term of this patent is extended or adjusted under 35 U.S.C. 154(b) by 260 days.

(21) Appl. No.: 17/559,449

(22) Filed: Dec. 22, 2021

(65) Prior Publication Data

US 2022/0209934 A1    Jun. 30, 2022

Related U.S. Application Data

(60) Provisional application No. 63/132,310, filed on Dec. 30, 2020.

(51) Int. Cl.
*H04L 9/00* (2022.01)
*G16B 50/40* (2019.01)

(52) U.S. Cl.
CPC .............. *H04L 9/008* (2013.01); *G16B 50/40* (2019.02); *H04L 2209/34* (2013.01)

(58) Field of Classification Search
CPC . H04L 9/008; H04L 2209/34; H04L 2209/88; G16B 50/40
See application file for complete search history.

(56) References Cited

U.S. PATENT DOCUMENTS

| | | | | |
|---|---|---|---|---|
| 9,900,147 | B2* | 2/2018 | Laine | H04L 9/0618 |
| 10,075,289 | B2* | 9/2018 | Laine | G09C 1/00 |
| 10,153,894 | B2* | 12/2018 | Laine | G06F 7/483 |
| 10,296,709 | B2* | 5/2019 | Laine | G16B 50/30 |
| 2008/0133474 | A1* | 6/2008 | Hsiao | G16B 30/00 |
| 2009/0319577 | A1* | 12/2009 | Obasanjo | G06Q 10/10 |
| 2014/0075183 | A1* | 3/2014 | Wang | G16B 30/00 |
| | | | | 713/150 |
| 2015/0154406 | A1* | 6/2015 | Naehrig | G06F 21/602 |
| | | | | 713/165 |

(Continued)

*Primary Examiner* — J. Brant Murphy
(74) *Attorney, Agent, or Firm* — Moore & Van Allen PLLC (57) ABSTRACT

A system is provided for encoding genomics data for secure storage and processing. In particular, the system may comprise a client and server operating environment that uses a unique encoding algorithm to transform genomics data and/or metadata to produce encoded genomics data and/or metadata. In some embodiments, the encoded genomics data and/or metadata may be encrypted using one or more encryption algorithms. The encoded and/or encrypted genomics data may be stored on a secure server (e.g., a cloud environment) that may perform subsequent processing steps on the encoded and/or encrypted genomics data. Once the processing steps have been completed, the server may transmit one or more outputs associated with the genomics data and/or metadata to a client device. In this way, the system provides an efficient and secure way to store and process genomics data.

12 Claims, 4 Drawing Sheets

(56) References Cited

U.S. PATENT DOCUMENTS

| | | | |
|---|---|---|---|
| 2015/0236849 A1* | 8/2015 | Ayday .................... | G16B 50/00 |
| | | | 713/193 |
| 2016/0105402 A1* | 4/2016 | Soon-Shiong ...... | H04L 63/0428 |
| | | | 713/164 |
| 2016/0224735 A1* | 8/2016 | Ayday .................... | G16B 50/30 |
| 2016/0275308 A1* | 9/2016 | Hubaux ................. | G16B 50/00 |
| 2017/0344646 A1* | 11/2017 | Antonopoulos ...... | H04L 63/205 |
| 2017/0357749 A1* | 12/2017 | Laine .................... | G16B 50/40 |
| 2019/0177719 A1* | 6/2019 | Glusman ............... | G16B 35/10 |
| 2020/0151356 A1* | 5/2020 | Rohloff ............... | G06F 21/6227 |
| 2022/0293222 A1* | 9/2022 | Paillier .................. | H04L 9/008 |
| 2023/0094541 A1* | 3/2023 | Gai ........................ | G06F 16/13 |
| | | | 713/189 |

* cited by examiner

| Chrom | Pos | Ref | Alt | Sample | Phase |
|---|---|---|---|---|---|
| 20 | 230496 | G | C | 1\|1 | 230496 |
| 20 | 258289 | A | T | 1\|0 | 230496 |
| 21 | 349741 | C | G | 1\|0 | |
| 19 | 45411941 | T | C | 0\|1 | 4356 |
| 19 | 45412079 | C | T | 1\|0 | 4356 |

Group 1: rows 1–2
Group 2: row 3
Group 3: rows 4–5

SYSTEM FOR ENCODING GENOMICS DATA FOR SECURE STORAGE AND PROCESSING

CROSS-REFERENCE TO RELATED APPLICATIONS

This application claims the benefit of U.S. Provisional Application No. 63/132,310, filed Dec. 30, 2020 and entitled "SYSTEM FOR ENCODING GENOMICS DATA FOR SECURE STORAGE AND PROCESSING," which is hereby incorporated by reference in its entirety.

GOVERNMENT LICENSE RIGHTS

This invention was made with government support under HG010978 awarded by the National Institutes of Health. The government has certain rights in the invention.

FIELD OF THE INVENTION

The present disclosure embraces a system, computer program product, and computer-implemented method for encoding genomics data for secure storage and processing.

BACKGROUND

There is a need for a computationally efficient, expedient, and secure way to encode, store, and process genomics data.

BRIEF SUMMARY

The following presents a simplified summary of one or more embodiments of the invention in order to provide a basic understanding of such embodiments. This summary is not an extensive overview of all contemplated embodiments and is intended to neither identify key or critical elements of all embodiments, nor delineate the scope of any or all embodiments. Its sole purpose is to present some concepts of one or more embodiments in a simplified form as a prelude to the more detailed description that is presented later.

A system is provided for encoding genomics data for secure storage and processing. In particular, the system may comprise a client and server operating environment that uses a unique encoding algorithm to transform genomics data and/or metadata to produce encoded genomics data and/or metadata. In some embodiments, the encoded genomics data and/or metadata may further be encrypted using one or more encryption algorithms. The encoded and/or encrypted genomics data may be stored on a secure server (e.g., a cloud environment) that may perform subsequent processing steps on the encoded and/or encrypted genomics data. Once the processing steps have been completed, the server may transmit one or more outputs associated with the genomics data and/or metadata to a client device. In this way, the system provides an efficient and secure way to store and process genomics data.

Accordingly, embodiments of the present disclosure provide a system for encoding genomics data for secure storage and processing, the system comprising a memory device with computer-readable program code stored thereon; a communication device; and a processing device operatively coupled to the memory device and the communication device, wherein the processing device is configured to execute the computer-readable program code to receive a set of genomic data; receive a set of genomic queries; encode, using an encoding algorithm, the set of genomic data to produce an encoded set of genomic data; and encode, using the encoding algorithm, the set of genomic queries to produce an encoded set of genomic queries, wherein executing the encoding algorithm comprises generating one or more vectors for one or more key variants associated with the set of genomic data; and generating, based on the set of genomic queries, one or more computations on the one or more vectors.

In some embodiments, the computer-readable program code, when executed, further causes the processing device to encrypt, using an encryption algorithm, the encoded set of genomics data to produce an encrypted set of genomic data; encrypt, using the encryption algorithm, the encoded set of genomic queries to produce an encrypted set of genomic queries; and transmit the encrypted set of genomic data and the encrypted set of genomic queries to a genomic data processing computing device.

In some embodiments, the encryption algorithm is a homomorphic encryption algorithm.

In some embodiments, the computer-readable program code, when executed, further causes the processing device to receive an output from the genomic data processing computing device, wherein the output comprises an analysis of the encrypted set of genomic data based on the encrypted set of genomic queries, wherein the output is encrypted using the encryption algorithm; and decrypt the output using a private key associated the encryption algorithm.

In some embodiments, the encoding algorithm comprises a phased encoding scheme.

In some embodiments, the encoding algorithm comprises an unphased encoding scheme.

Embodiments of the present disclosure provide a computer program product for encoding genomics data for secure storage and processing, the computer program product comprising at least one non-transitory computer readable medium having computer-readable program code portions embodied therein, the computer-readable program code portions comprising executable code portions for receiving a set of genomic data; receiving a set of genomic queries; encoding, using an encoding algorithm, the set of genomic data to produce an encoded set of genomic data; and encoding, using the encoding algorithm, the set of genomic queries to produce an encoded set of genomic queries, wherein executing the encoding algorithm comprises generating one or more vectors for one or more key variants associated with the set of genomic data; and generating, based on the set of genomic queries, one or more computations on the one or more vectors.

In some embodiments, the computer-readable program code portions further comprise executable portions for encrypting, using an encryption algorithm, the encoded set of genomics data to produce an encrypted set of genomic data; encrypting, using the encryption algorithm, the encoded set of genomic queries to produce an encrypted set of genomic queries; and transmitting the encrypted set of genomic data and the encrypted set of genomic queries to a genomic data processing computing device.

In some embodiments, the encryption algorithm is a homomorphic encryption algorithm.

In some embodiments, the computer-readable program code portions further comprise executable portions for receiving an output from the genomic data processing computing device, wherein the output comprises an analysis of the encrypted set of genomic data based on the encrypted set of genomic queries, wherein the output is encrypted using the encryption algorithm; and decrypting the output using a private key associated the encryption algorithm.

In some embodiments, the encoding algorithm comprises a phased encoding scheme.

In some embodiments, the encoding algorithm comprises an unphased encoding scheme.

Embodiments of the present disclosure also provide a computer-implemented method for encoding genomics data for secure storage and processing, the computer-implemented method comprising receiving a set of genomic data; receiving a set of genomic queries; encoding, using an encoding algorithm, the set of genomic data to produce an encoded set of genomic data; and encoding, using the encoding algorithm, the set of genomic queries to produce an encoded set of genomic queries, wherein executing the encoding algorithm comprises generating one or more vectors for one or more key variants associated with the set of genomic data; and generating, based on the set of genomic queries, one or more computations on the one or more vectors.

In some embodiments, the computer-implemented method further comprises encrypting, using an encryption algorithm, the encoded set of genomics data to produce an encrypted set of genomic data; encrypting, using the encryption algorithm, the encoded set of genomic queries to produce an encrypted set of genomic queries; and transmitting the encrypted set of genomic data and the encrypted set of genomic queries to a genomic data processing computing device.

In some embodiments, the encryption algorithm is a homomorphic encryption algorithm.

In some embodiments, the computer-implemented method further comprises receiving an output from the genomic data processing computing device, wherein the output comprises an analysis of the encrypted set of genomic data based on the encrypted set of genomic queries, wherein the output is encrypted using the encryption algorithm; and decrypting the output using a private key associated the encryption algorithm.

In some embodiments, the encoding algorithm comprises a phased encoding scheme.

In some embodiments, the encoding algorithm comprises an unphased encoding scheme.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Having thus described embodiments of the invention in general terms, reference will now be made to the accompanying drawings, wherein:

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to elements throughout. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein.

"The system" as used herein may refer to the computing systems, devices, software, applications, hardware, and/or other resources that may perform the various functions as described herein. Accordingly, the system may comprise desktop computers, laptop computers, servers, Internet-of-Things ("IoT") devices, networked terminals, mobile smartphones, smart devices (e.g., smart watches), network connections, and/or other types of computing systems or devices and/or peripherals along with their associated applications. The system may also be referred to herein as the genomic archiving and communications system ("GACS").

"Computing system" or "computing device" as used herein may refer to a networked computing device within the entity system. The computing system may include a processor, a non-transitory storage medium, a communications device, and a display. The computing system may be configured to support user logins and inputs from any combination of similar or disparate devices. Accordingly, the computing system may be a portable electronic device such as a smartphone, tablet, single board computer ("SBC"), system on a chip ("SoC"), smart device, or laptop. In other embodiments, the computing system may be a stationary unit such as a personal desktop computer, networked terminal, IoT device, or the like.

"User" as used herein may refer to an individual who may interact with the system to access the functions therein. In some embodiments, the user may be a healthcare professional (e.g., a physician) who may use the system for the purposes of clinical decisioning.

Accordingly, the term "user device" or "mobile device" may refer to mobile phones, personal computing devices, tablet computers, wearable devices, and/or any stationary or portable electronic device capable of processing, receiving, transmitting, and/or storing data therein.

"Encoding" or "encoding algorithm" as used herein may refer to a set of logical and/or mathematical operations or processes to generate an alternative representation of an original data input. In particular, encoding may refer to the process of generating an encoded output (e.g., a numerical representation) of input genomics data and/or metadata as described in further detail herein.

"Encryption" or "encryption algorithm" as used herein may refer to a set of logical and/or mathematical operations or processes to convert input data into ciphertext. Accordingly, "encrypting" as used herein may refer to the process of producing an encrypted output based on a data input into an encryption algorithm. In some embodiments, the encryption algorithm may be a homomorphic encryption algorithm that allows computing systems to perform computations on data encrypted using the homomorphic encryption algorithm. In such embodiments, the output of the computations performed on the encrypted data, when decrypted, may be the same as if such computations had been performed on the decrypted data. "Homomorphic encryption" may also be referred to herein as "HE."

"Cryptographic hash function" or "hash algorithm" as used herein may refer to a set of logical and/or mathematical operations or processes (e.g., an encryption algorithm) that may be executed on a specified segment of data to produce a hash output. Given a specified data input, the hash algorithm may produce a cryptographic hash output value which is a fixed-length character string. Examples of such hash algorithms may include MD5, Secure Hash Algorithm/SHA, or the like. Accordingly, "hashing" as used herein may refer to the process of producing a hash output based on a data input into a hash algorithm.

"Key" or "cryptographic key" as used herein may refer to data (e.g., a character string) which determines the manner in which an input is transformed into an output using a cryptographic algorithm (e.g., an encryption algorithm). Accordingly, "symmetric cryptography" or "symmetric key cryptography" may refer to a process for data encryption by which multiple users and/or devices use the same key to encrypt communications.

"Public-key cryptography" or "asymmetric cryptography" may refer to a process for data encryption and/or verification by which a pair of asymmetric corresponding cryptographic keys are generated (e.g., a "key pair" comprising a "public key" intended to be distributed and a "private key" intended to be possessed by a single user or device). Data encrypted using a public key may be decrypted only by the possessor of the corresponding private key. Furthermore, data signed with a private key may be validated by the possessor of the corresponding public key to verify the identity of the signer (which may be referred to herein as "digital signing"). In one embodiment, a set of encoded genomic data may be encrypted using a public key associated with the person with whom the genomic data is associated (e.g., a patient).

In the context of genomics, new discoveries are being made at a fast pace, linking genetic variants with disease risk and drug interactions. As next-generation genome sequencing becomes more reliable, economical, and widely available, the findings from research are being incorporated into clinical practice. Making responsible and meaningful use of human genomic data to support healthcare, including clinical decision support ("CDS") applications, is an emerging challenge of great importance. CDS can provide answers to questions such as: 'what is the patient's CYP2C19 genotype and drug-metabolism phenotype', and 'does the patient have any pathogenic BRCA1 variants'. Accordingly, the questions to be answered by processing genomic data may be referred to herein as "CDS questions."

Genome data are large, comprising billions of base-pairs on thousands of genes and intergenic regions. Next-generation sequencing can identify thousands to millions of variants, whose clinical significance can change over time as knowledge evolves. Sequencing can produce gigabytes of data for a single individual. It is impractical to securely store and analyze such large data in contemporary health record systems, which clinicians use when delivering care to patients. The challenges for storage can be more acute for smaller healthcare facilities that may not have large, secure data repositories.

Furthermore, the storage of genome data increases privacy concerns. Theft and misuse of genome data can cause long-term harm to individuals and their families because the data are unique, heritable, and immutable. Given this highly-sensitive nature of genome data, appropriately strict levels of protection must be applied to their storage. Accordingly, there is a need for an efficient and secure way to store and process genomics data to drive clinical decisioning.

Accordingly, the present disclosure provides a system for encoding genomics data for secure storage and processing. In particular, the system may comprise one or more client computing devices and/or server computing devices to perform the various processes described herein. To illustrate, a first client computing device (e.g., a computing device owned and/or operated by an entity that performs genome sequencing) may perform sequencing of genome data associated with a patient and subsequently perform encoding of the genome data. A second client computing device (e.g., a computing device owned and/or operated by a healthcare professional or entity) may be used to generate one or more CDS questions about the genome data. In some embodiments, metadata associated with the genomics data (e.g., patient information) and/or the CDS questions may also be encoded using the algorithm.

Subsequently, the encoded genomics data, metadata, and/or CDS questions may be encrypted using an encryption algorithm (e.g., a homomorphic encryption algorithm) using a cryptographic key associated with the genomics data and/or the patient. In embodiments in which asymmetric cryptography is used, the genomics data may be encrypted using a public key associated with the genomics data and/or the patient. In this way, the cloud server may be unable to decrypt the genome data stored therein. Furthermore, in some embodiments, particularly sensitive genomics metadata may further be encrypted and/or hashed (e.g., patient data may be hashed before being encoded and/or encrypted). A lookup table for the genomic data and/or metadata may be stored on the client computing device to further protect against the server gaining access to the sensitive data therein.

Once encoded and/or encrypted, the genomics data, metadata, and/or CDS questions may be transmitted to a server over a network for subsequent processing. In embodiments in which homomorphic encryption is used, the server stores the encrypted data and performs the computations without decrypting the data or the CDS questions. The results may then be returned to the first and/or second client computing devices to be decrypted using a private key corresponding to the public key. Only the custodian of the data, (e.g., the client that has the private key), can decrypt results. In some embodiments, the keys used to encrypt and/or decrypt data may be stored in a secure keystore, which may be a repository of public and/or private keys to be used by a custodian entity (e.g., a hospital associated with the patient). The system as described herein may retrieve key variants, calculate genotypes, and compute phenotypes based on genotype-matching or scoring. "Key variant" as used herein may refer to known variants that are of interest for a given scenario (e.g., because they are known to be associated with a disease or with altered drug metabolism).

An exemplary embodiment is provided for illustrative purposes. In such an embodiment, a physician of a patient may wish to analyze genome data associated with the patient to determine whether the patient has a particular variant of a target gene. The physician may order the sequencing of the genome data (e.g., with a laboratory that performs sequencing of genomics data). The laboratory may sequence the genome data and subsequently encode and encrypt the data as described in further detail herein (e.g., using a public key). The encoded and encrypted data may be transmitted from the laboratory to a cloud server which may host genomic data. Furthermore, the physician may, via a computing device associated with the physician, transmit one or more CDS questions regarding the patient's genome data to the cloud server, where the CDS questions may also be encoded and encrypted. The cloud server may then perform an analysis of the encoded and encrypted genome data and transmit encrypted outputs of the analysis to the physician's computing device. The physician's computing device may then decrypt the encrypted analysis using a private cryptographic key associated with the public key.

The system as described herein confers a number of technological advantages over existing technologies for genomic data processing. In particular, by using the encoding algorithm as described herein, the system provides an expedient way to represent genomic data and allow the genomic data to be processed efficiently. Furthermore, by using the encryption schemes and/or system architectures described herein, the system provides a way to harness the vast computing power and resources of genomic data servers while preserving the security and privacy of the sensitive data being stored and/or processed.

It will be appreciated by those skilled in the art that the foregoing embodiments are provided for illustrative purposes only and are not intended to limit the scope of the disclosure as provided herein. For instance, though the above embodiment describes the use of two client computing devices, it is within the scope of the disclosure for the above processes to be performed on a fewer or greater number of client computing devices (e.g., the genome data and CDS questions may be encoded and/or encrypted by a single client computing device). Furthermore, it should be appreciated that the disclosure provided herein may also be applicable to areas or use cases outside of the clinical care context (e.g., for research purposes).

Figure 1:
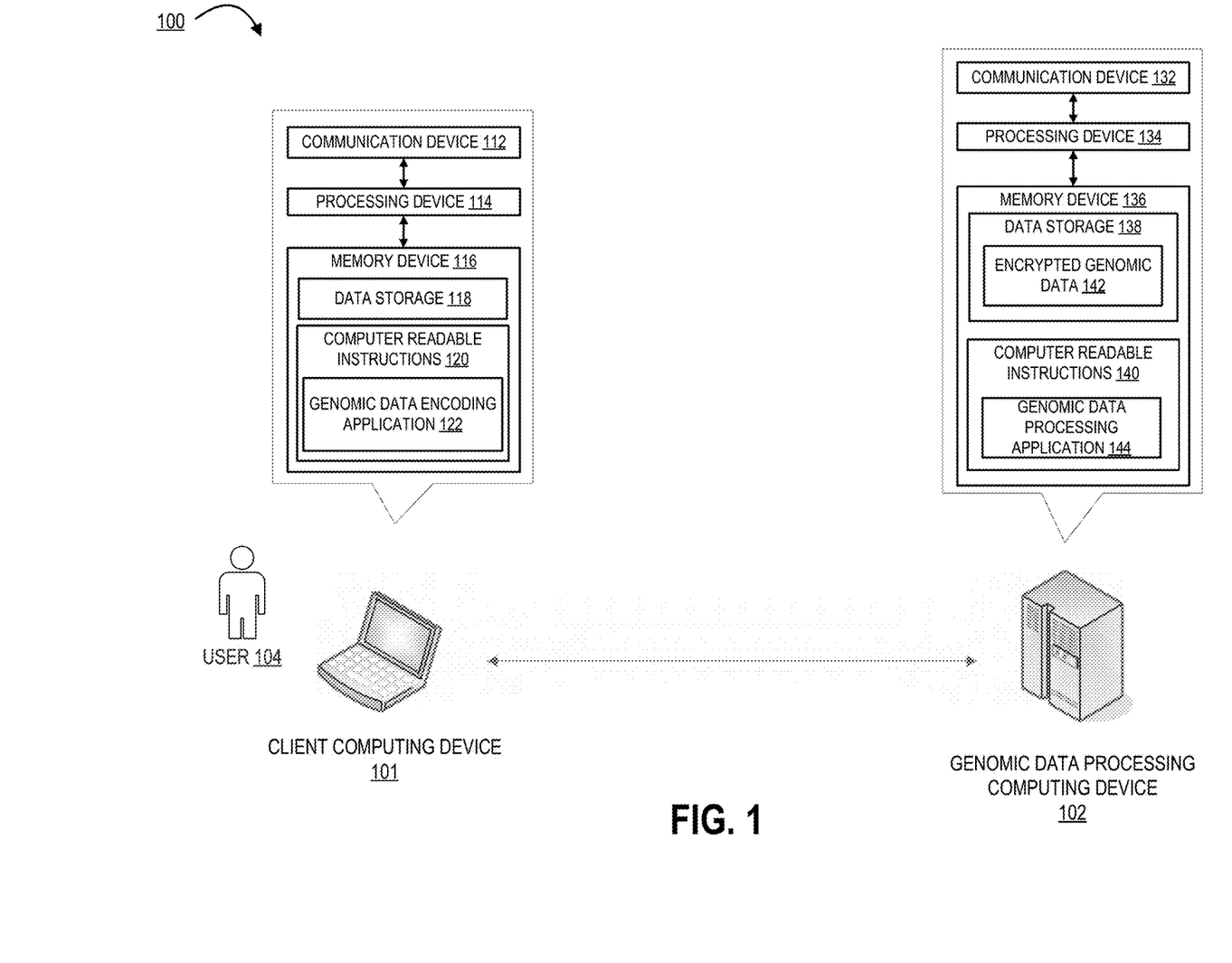
FIG. 1 illustrates an operating environment for the system, in accordance with some embodiments of the present disclosure.

Turning now to the figures, FIG. 1 illustrates an operating environment 100 for the system described herein, in accordance with one embodiment of the present disclosure. In particular, FIG. 1 illustrates a client computing device 101 that is operatively coupled, via a network, to a genomic data processing computing device 102. In such a configuration, the client computing device 101 may transmit information to and/or receive information from the genomic data processing computing device 102. It should be understood that FIG. 1 illustrates only an exemplary embodiment of the operating environment 100, and it will be appreciated that the operating environment 100 may comprise a fewer or greater number of computing systems and/or devices than are depicted in FIG. 1. For example, though the FIG. 1 depicts a single client computing device 101 and a single genomic data processing computing device 102, alternative embodiments may comprise multiple client computing devices communicatively coupled with multiple genomic data processing computing devices. It should also be understood that one or more functions of the systems, devices, or servers as depicted in FIG. 1 may be combined into a single system, device, or server.

The network may be a system specific distributive network receiving and distributing specific network feeds and identifying specific network associated triggers. The network may include one or more cellular radio towers, antennae, cell sites, base stations, telephone networks, cloud networks, radio access networks (RAN), Wi-Fi networks, or the like. Additionally, the network may also include a global area network (GAN), such as the Internet, a wide area network (WAN), a local area network (LAN), or any other type of network or combination of networks. Accordingly, the network may provide for wireline, wireless, or a combination wireline and wireless communication between devices on the network.

As illustrated in FIG. 1, the client computing device 101 may be a networked server, desktop computer, laptop computer, routing device, or other type of computing system within the network environment which performs the encoding and/or encryption of genomic data, metadata, and/or CDS questions, as described herein. Accordingly, the client computing device 101 may comprise a processing device 114 operatively coupled to a communication device 112 and a memory device 116 having data storage 118 and computer readable instructions 120 stored thereon.

As used herein, the term "processing device" generally includes circuitry used for implementing the communication and/or logic functions of the particular system. For example, a processing device may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. The processing device may include functionality to operate one or more software programs based on computer-readable instructions thereof, which may be stored in a memory device.

The processing device 114 of the client computing device 101 may use the communication device 112 to communicate with the network and other devices on the network, such as, but not limited to the genomic data processing computing device 102. Accordingly, the communication device 112 generally comprises one or more hardware components such as a modem, antennae, Wi-Fi or Ethernet adapter, radio transceiver, or other device for communicating with other devices on the network.

In some embodiments, the data storage 118 of the memory device 116 stores data related to the system environment (e.g., genomic sequencing data, patient information, or the like). Furthermore, the computer-readable instructions 120 of the memory device 116 may comprise a genomic data encoding application 122, which may comprise computer-executable program code that instructs the processing device 114 to perform certain logic, data processing, and/or data storing functions of the genomic data encoding application 122. For instance, the genomic data encoding application 122 may read genomic data and/or metadata and/or CDS questions as inputs and to produce the encoded and/or encrypted copies thereof.

In some embodiments, the client computing device 101 may be a computing system that is operated by a user 104 (e.g., a physician or laboratory technician). In such embodiments, the client computing device 101 may comprise a user interface comprising one or more input devices (e.g., a keyboard, keypad, microphone, mouse, tracking device, biometric readers, capacitive sensors, or the like) and/or output devices (e.g., a display such as a monitor, projector, headset, touchscreen, and/or auditory output devices such as speakers, headphones, or the like) for receiving inputs from and/or providing outputs to the user 104.

As further illustrated in FIG. 1, the operating environment 100 may further comprise a genomic data processing computing device 102 in operative communication with the client computing device 101. In particular, the genomic data processing computing device 102 may be a computing device which receives encrypted data from the client computing device 101 for storage and subsequent processing. Accordingly, the genomic data processing computing device 102 may be a computing system such as a server or networked terminal, though it is within the scope of the disclosure for the genomic data processing computing device 102 to be a device such as a desktop computer, laptop, IoT device, smartphone, tablet, single-board computer, or the like.

The genomic data processing computing device 102 may comprise a processing device 134 operatively coupled to a communication device 132 and a memory device 136 having data storage 138 and computer readable instructions 140 stored thereon. The data storage 138 may comprise encrypted genomic data 142, which may have been received from the client computing device 101. In this regard, the genomic data processing computing device 102 may, using a genomic data processing application 144 stored within the computer readable instructions 140, perform one or more process or operations on the encrypted genomic data 142 according to the encoded and/or encrypted CDS questions received from the client computing device 101.

The communication devices as described herein may comprise a wireless local area network (WLAN) such as Wi-Fi based on the Institute of Electrical and Electronics Engineers' (IEEE) 802.11 standards, Bluetooth short-wavelength UHF radio waves in the ISM band from 2.4 to 2.485 GHz or other wireless access technology. Alternatively or in addition to the wireless interface, the computing systems may also include a communication interface device that may be connected by a hardwire connection to the resource distribution device. The interface device may comprise a connector such as a USB, SATA, PATA, SAS or other data connector for transmitting data to and from the respective computing system.

The computing systems described herein may each further include a processing device communicably coupled to devices as a memory device, output devices, input devices, a network interface, a power source, a clock or other timer, a camera, a positioning system device, a gyroscopic device, one or more chips, and the like.

In some embodiments, the computing systems may access one or more databases or datastores (not shown) to search for and/or retrieve information related to the service provided by the entity. The computing systems may also access a memory and/or datastore local to the various computing systems within the operating environment 100.

The processing devices as described herein may include functionality to operate one or more software programs or applications, which may be stored in the memory device. For example, a processing device may be capable of operating a connectivity program, such as a web browser application. In this way, the computing systems may transmit and receive web content, such as, for example, product valuation, service agreements, location-based content, and/or other web page content, according to a Wireless Application Protocol (WAP), Hypertext Transfer Protocol (HTTP), and/or the like.

A processing device may also be capable of operating applications. The applications may be downloaded from a server and stored in the memory device of the computing systems. Alternatively, the applications may be pre-installed and stored in a memory in a chip.

The chip may include the necessary circuitry to provide integration within the devices depicted herein. Generally, the chip will include data storage which may include data associated with the service that the computing systems may be communicably associated therewith. The chip and/or data storage may be an integrated circuit, a microprocessor, a system-on-a-chip, a microcontroller, or the like. In this way, the chip may include data storage. Of note, it will be apparent to those skilled in the art that the chip functionality may be incorporated within other elements in the devices. For instance, the functionality of the chip may be incorporated within the memory device and/or the processing device. In a particular embodiment, the functionality of the chip is incorporated in an element within the devices. Still further, the chip functionality may be included in a removable storage device such as an SD card or the like.

A processing device may be configured to use the network interface to communicate with one or more other devices on a network. In this regard, the network interface may include an antenna operatively coupled to a transmitter and a receiver (together a "transceiver"). The processing device may be configured to provide signals to and receive signals from the transmitter and receiver, respectively. The signals may include signaling information in accordance with the air interface standard of the applicable cellular system of the wireless telephone network that may be part of the network. In this regard, the computing systems may be configured to operate with one or more air interface standards, communication protocols, modulation types, and access types. By way of illustration, the devices may be configured to operate in accordance with any of a number of first, second, third, fourth, and/or fifth-generation communication protocols and/or the like. For example, the computing systems may be configured to operate in accordance with second-generation (2G) wireless communication protocols IS-136 (time division multiple access (TDMA)), GSM (global system for mobile communication), and/or IS-95 (code division multiple access (CDMA)), or with third-generation (3G) wireless communication protocols, such as Universal Mobile Telecommunications System (UMTS), CDMA2000, wideband CDMA (WCDMA) and/or time division-synchronous CDMA (TD-SCDMA), with fourth-generation (4G) wireless communication protocols, with fifth-generation (5G) wireless communication protocols, or the like. The devices may also be configured to operate in accordance with non-cellular communication mechanisms, such as via a wireless local area network (WLAN) or other communication/data networks.

The network interface may also include an application interface in order to allow a user or service provider to execute some or all of the above-described processes. The application interface may have access to the hardware, e.g., the transceiver, and software previously described with respect to the network interface. Furthermore, the application interface may have the ability to connect to and communicate with an external data storage on a separate system within the network.

The devices may have an interface that includes user output devices and/or input devices. The output devices may include a display (e.g., a liquid crystal display (LCD) or the like) and a speaker or other audio device, which are operatively coupled to the processing device. The input devices, which may allow the devices to receive data from a user, may include any of a number of devices allowing the devices to receive data from a user, such as a keypad, keyboard, touch-screen, touchpad, microphone, mouse, joystick, other pointer device, button, soft key, and/or other input device(s).

The devices may further include a power source. Generally, the power source is a device that supplies electrical energy to an electrical load. In some embodiment, power source may convert a form of energy such as solar energy, chemical energy, mechanical energy, or the like to electrical energy. Generally, the power source may be a battery, such as a lithium battery, a nickel-metal hydride battery, or the like, that is used for powering various circuits, e.g., the transceiver circuit, and other devices that are used to operate the devices. Alternatively, the power source may be a power adapter that can connect a power supply from a power outlet to the devices. In such embodiments, a power adapter may be classified as a power source "in" the devices.

As described above, the computing devices as shown in FIG. 1 may also include a memory device operatively coupled to the processing device. As used herein, "memory" may include any computer readable medium configured to store data, code, or other information. The memory device may include volatile memory, such as volatile Random Access Memory (RAM) including a cache area for the temporary storage of data. The memory device may also include non-volatile memory, which can be embedded and/or may be removable. The non-volatile memory may additionally or alternatively include an electrically erasable programmable read-only memory (EEPROM), flash memory or the like.

The memory device may store any of a number of applications or programs which comprise computer-executable instructions/code executed by the processing device to implement the functions of the devices described herein.

The computing systems may further comprise a gyroscopic device. The positioning system, input device, and the gyroscopic device may be used in correlation to identify phases within a service term.

Each computing system may also have a control system for controlling the physical operation of the device. The control system may comprise one or more sensors for detecting operating conditions of the various mechanical and electrical systems that comprise the computing systems or of the environment in which the computing systems are used. The sensors may communicate with the processing device to provide feedback to the operating systems of the device. The control system may also comprise metering devices for measuring performance characteristics of the computing systems. The control system may also comprise controllers such as programmable logic controllers (PLC), proportional integral derivative controllers (PID) or other machine controllers. The computing systems may also comprise various electrical, mechanical, hydraulic or other systems that perform various functions of the computing systems. These systems may comprise, for example, electrical circuits, motors, compressors, or any system that enables functioning of the computing systems.

Figure 2:
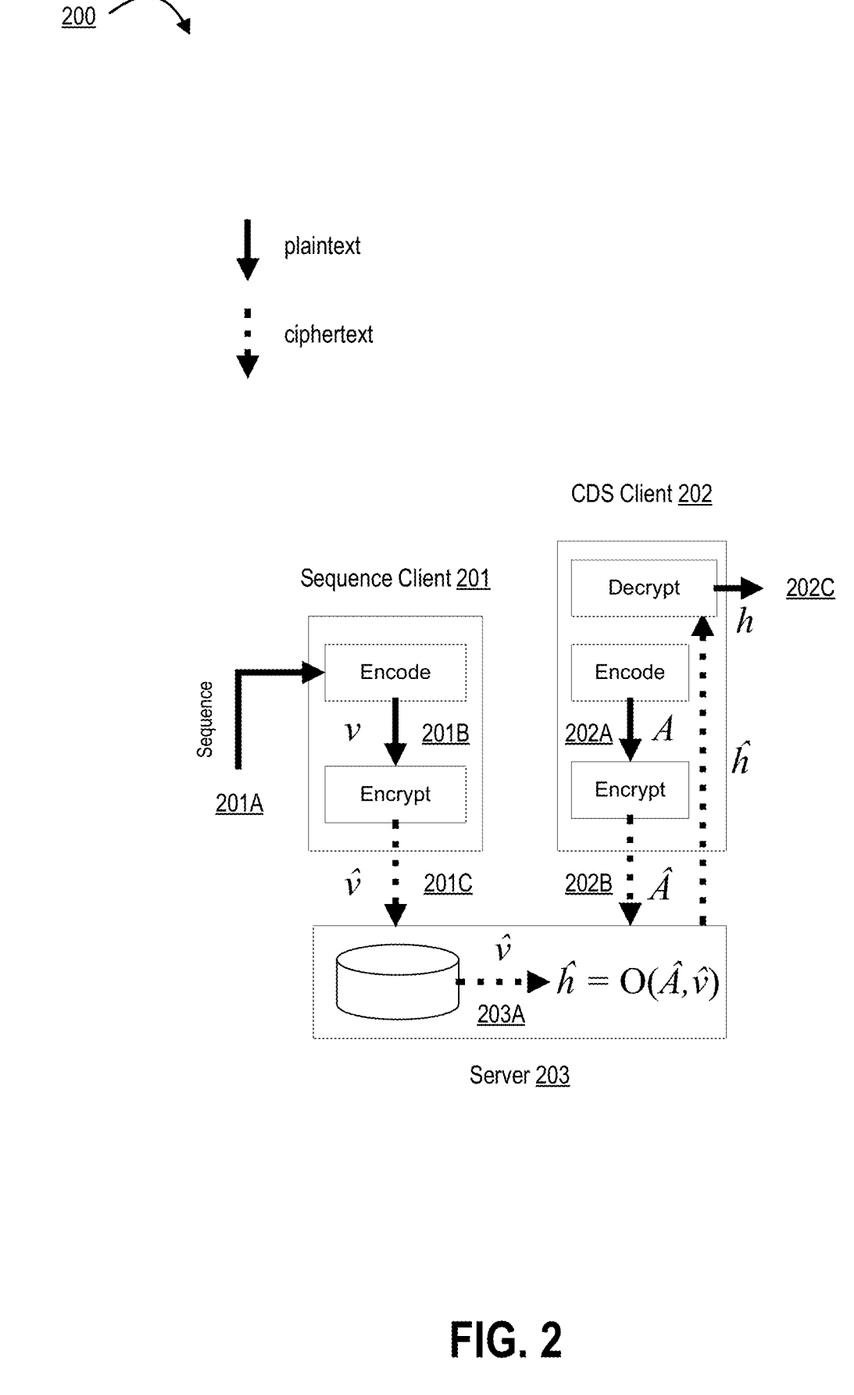
FIG. 2 illustrates a process flow for encoding genomics data for secure storage and processing, in accordance with some embodiments of the present disclosure.

FIG. 2 illustrates a process flow 200 for encoding genomics data for secure storage and processing, in accordance with some embodiments of the present disclosure. The input data may comprise variant call format (VCF) files, which may be text files containing sequenced genomic data. Since computation requires numerical representation, the sequence client 201 (e.g., the client computing device as shown in FIG. 1) may receive the input data at step 201A, and subsequently encode the variants from a VCF file as a vector shown as v, at step 201B. The sequence client 201 may also be referred to herein as an "encryption client." The VCF files may be provided to the sequence client 201 through, for instance, a sequencing pipeline or other source of genomic data. At step 201C, the variant vector may be homomorphically encrypted (shown as P) and sent to a server 203 (e.g., the genomic data processing computing device 102 as shown in FIG. 1) for storage. Patient and sequence identifiers may be metadata that are deterministically encrypted before being sent to the server 203 for storage to conceal them from the server.

Questions or queries (e.g., CDS questions) may be received (e.g., through a clinical application such as a clinical decision support system) by a CDS client 202 (e.g., another client computing device 101). The CDS client 202 may also be referred to herein as a "query client." The CDS client 202 may, at step 202A, encode the question as a matrix or vector A, encrypt it to Â at step 202B, along with the deterministically encrypted patient identifiers and send the encrypted question to the server 203. The server 203 may compute a result ĥ at step 203A and send such result to the CDS client 202 at step 203B for decryption by the CDS client 202 to h at step 202C. In such scenarios, the result h may be the same (within a noise margin defined by the precision parameter) as the unencrypted computation on the plain data, O(A, v). Accordingly, the process and architecture of the system may be configured such that the data, questions or results are not decrypted by the server.

The system may define one or more operations that can be used by CDS systems to obtain variants or calculate genotypes (e.g., pairs of haplotypes). These operations include weighted summation of variants and evaluation of zygosity (e.g., heterozygous or homozygous). Haplotyping includes a special case of finding a particular haplotype, e.g., in the clinical trial application. For the pharmacogenomics application, the system may compute a phenotype from the genotype using the client computing device.

Encryption Client

The encryption client ("EC") may be installed in a client environment (e.g., a hospital), either in their local data center or in their cloud account. In some embodiments, the EC may be packaged in an "appliance" that can easily be installed at a hospital.

EC may provide an asynchronous REST API that may accept a VCF file (or a pointer to a VCF file) and other patient identification parameters. The API method may process the VCF file, converting it into a vector format, then encrypting the vector format data, and finally storing the converted VCF file in the GACS in the cloud. The EC may store an audit record of each request received.

Vector-Encoding of Key Variants

For computation over encryption, analysis questions must be expressed mathematically. Accordingly, the disclosure provides a novel framework to represent variant data and CDS questions numerically. In this framework, key variants are encoded as vectors, and the analysis questions are encoded as linear operations on these vectors. Each known key variant is represented by a fixed element in a vector. The variant and its element position in a vector are stored in a lookup table on the client. The presence of a variant is encoded by a "1" (one), and its absence is encoded by a "0" (zero). Pairs of vectors are created because chromosomes exist in pairs. Each vector-pair represents a region of the genome. There are groups of variants that can be considered together because they are in a particular region, define particular haplotypes, or determine phenotypes. In the model, it is optimal to encode such a group of variants into the same vector-pair. The encoding is done by the client before encryption.

Two types of encoding schemes may be used: "phased" and "unphased". Unphased encoding allows us to compute on variants. Unphased encoding is used when CDS does not need to calculate haplotypes (e.g., for LDLR variants). Phased encoding allows us to calculate haplotypes and genotypes in addition to computing on variants. Consider two key variants in the APOE gene as shown in the rightmost two columns of Table 1. Two variants can generate four haplotypes. If a patient has the heterozygous variant rs7412, the genotype is $\varepsilon_2/\varepsilon_3$. For this patient, a representative pair of vectors is [1, 0] and [0, 0].

| Haplotype | Phenotype | rs7412 | rs429358 |
|---|---|---|---|
| $\varepsilon_1$ (0.2%) | Normal risk | T | C |
| $\varepsilon_2$ (7%) | Decreased risk | T | T |
| $\varepsilon_3$ (wild type, 79%) | Normal risk | C | T |
| $\varepsilon_4$ (14%) | Increased risk | C | C |

Table 1 illustrates Haplotypes of the APOE gene. The phenotype column indicates haplotype-associated risk for development of Alzheimer's Disease. Haplotypes are determined by the alleles at rs7412 and rs429358 as shown.

Figure 3:
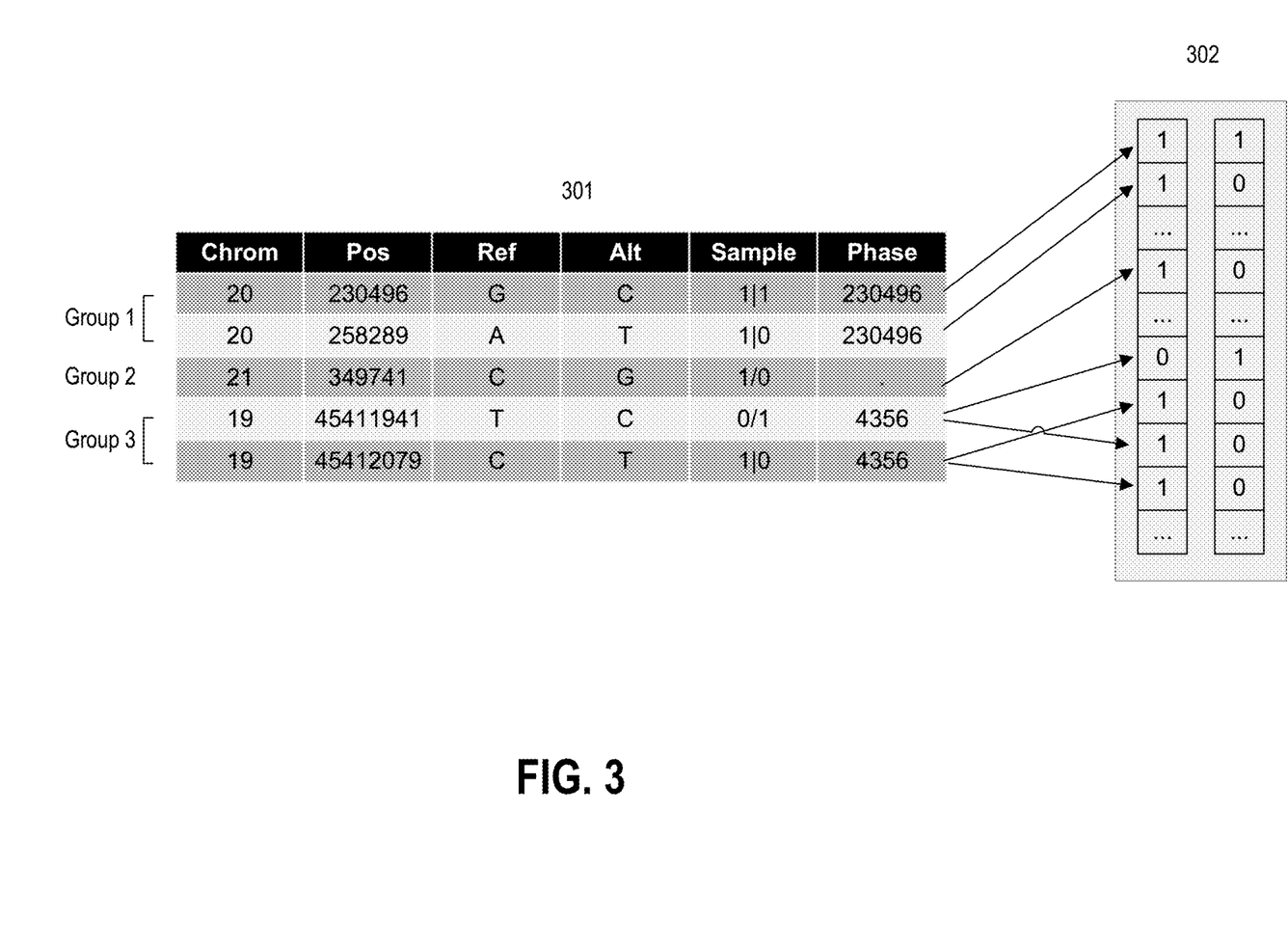
FIG. 3 is a diagram illustrating phased encoding of sequence data, according to some embodiments of the present disclosure.

FIG. 3 is a diagram illustrating phased encoding of sequence data, according to some embodiments of the present disclosure. The sequence data table 301 of FIG. 3 shows partially phased genome sequence data from a VCF file. In the Sample column, the pipe delimiters indicate phased variants and slashes indicate unphased variants. The unphased heterozygous data generates two combinations. A lookup table (not shown) is used to assign a variant to a vector and an element position in the vector to produce the encoded output 302.

When phase information is present in the VCF file, the pair of vectors is uniquely determined, although we may not know which is maternally or paternally derived. When phase information is absent or partial, and heterozygous variants are present, there are ambiguities regarding which homologous chromosome (e.g., maternally-vs. paternally-derived) has particular key variants. In other words, the haplotypes are uncertain. To accommodate ambiguity, multiple combinations of variants may be generated that capture all the possible haplotypes. If the patient had two unphased heterozygous variants, the vector pairs could be [1,0]/[0,1], representing $\varepsilon_2/\varepsilon_4$, or [1,1]/[0,0] representing $\varepsilon_1/\varepsilon_3$. In general, with P distinct or unknown phases, the number of combination pairs is $2^{P-1}$. Ambiguous genotype calls are often resolved clinically according to population probability distributions, which we anticipate occurring in the CDS client.

For efficient computation and storage, the combinations of variants (in a group of variants) are concatenated vertically within the pair of vectors. This allows us to efficiently pack the vectors into the ciphertexts, whose lengths are fixed by the multiplicative depth of the encryption circuit.

In unphased encoding, partial phase information from the VCF file may be ignored. When a heterozygous variant is present, the "1" may be into the relevant element in either vector of the pair. Here, we do not generate various combinations of unphased variants. Unphased encoding allows us to do variant-level operations, but it does not allow us to calculate genotypes, except for those genotypes defined by a single variant. For many CDS applications, unphased encoding is sufficient to answer the clinical question. An example is the application to determine the risk of FH, in which we need to detect the presence of certain variants in the LDLR gene. In this application, there are over 2000 variants and as many possible haplotypes. A possible combinatorial explosion of unphased variants is avoided by unphased encoding.

Computations on the Server

The analysis questions are framed as linear operations on vector data. This is because HE data are closed under addition and multiplication only. Surrogate solutions are sometimes necessary to frame analysis questions as linear operations. These solutions must balance complexity, memory, and the need to coordinate the computation with the client. The computations are of the forms $\hat{h}=\hat{A}\hat{v}$, $<\hat{a}, \hat{v}_1+\hat{v}_2>$ and $<\hat{a}, \hat{v}_1\otimes\hat{v}_2>$, where $\otimes$ represents element-wise multiplication. Logical operations (e.g., $<\hat{a}, \hat{v}_1$ OR $\hat{v}_2>$) and logical template matching are also allowed.

The plaintext operator A is a matrix whose rows are the haplotype template vectors, i.e., each row defines a particular haplotype. Each row of A is encrypted as a ciphertext. $\hat{h}=\hat{A}\ \hat{v}$ is calculated using dot-products. To calculate a dot-product the system may perform an element-wise multiplication followed by summation across the vector. Summation across the vector is performed by performing n left shifts and additions, where n is the power of two greater than or equal to the length of the plaintext vector, $n=\lceil\log_2|v|\rceil$. The plaintext equivalent vector h is a real number vector, and the patient haplotype corresponds to the element with the largest result. In such scenarios, a surrogate operation can be used or the result $\hat{h}$ can be returned to the client, which decrypts it to h and then computes argmax(h).

The above disclosure provides for encoding using the example of a two-element plaintext vector, v. In other embodiments (e.g., in the phased encoding method), elements may be added to v to include wildtypes, i.e., the absence of variants at key-variant positions. This is because different haplotypes have different numbers of variants, which means normalization by the number of variants is required. By including the wildtype elements, v has a constant amplitude, providing implicit normalization.

Figure 4:
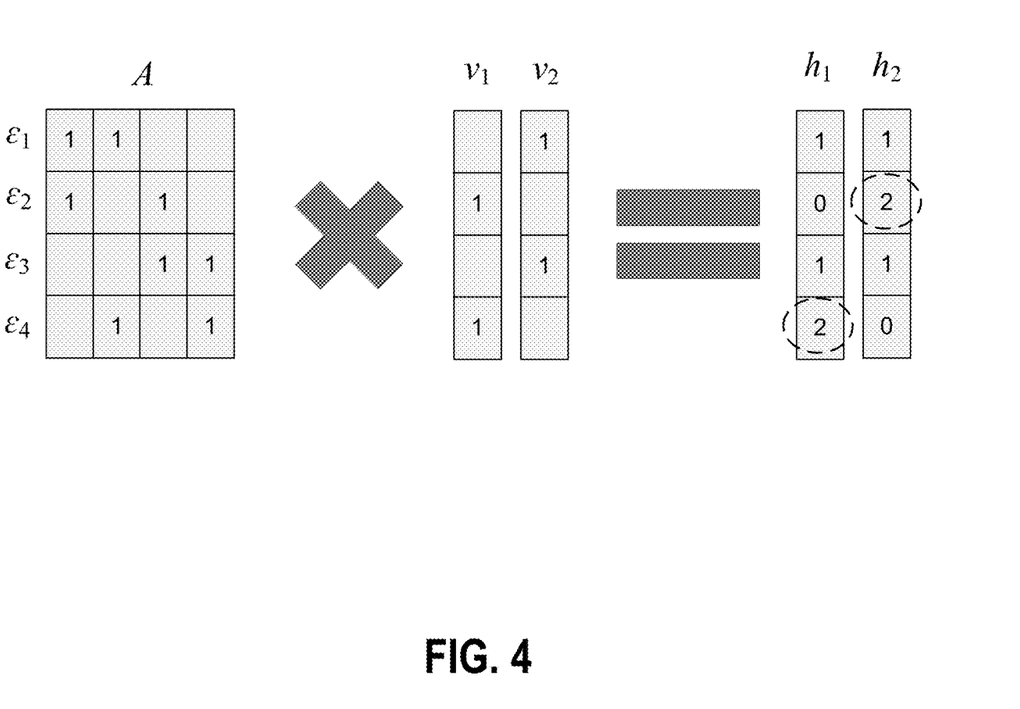
FIG. 4 is a diagram illustrating haplotyping of a pair of unambiguous vectors, in accordance with some embodiments of the present disclosure.

FIG. 4 is a diagram illustrating haplotyping of a pair of unambiguous vectors, in accordance with some embodiments of the present disclosure. In particular, FIG. 4 illustrates the Haplotypes for APOE found by argmax(Av). The rows of A are the haplotypes and the columns are variants. The zero-valued elements are shown blank for clarity. For the pair of variant vectors shown, $v_1$=[0 1 0 1] and $v_2$=[1 0 1 0], the genotype is $\varepsilon_4/\varepsilon_2$.

If the variant vector is ambiguous due to incomplete phasing, then the variant combinations may be stacked vertically before encryption. Since the dot-product uses shift and add operations, each combination is padded with zeros to the nearest power of two, to avoid contamination from the next combination. The CDS client replicates the matrix A horizontally to match the stacked v and encrypts it.

Logical Template Matching

Consider logical template matching to calculate haplotypes. Every known haptotype is represented by a template vector Logical template matching can be done with an element-wise XOR operation between a template vector end patient vector, followed by an OR operation across the result vector, and finally taking the ones complement. The result is "1" when the allele template vector and the patient vector are identical, and '0' otherwise, Given a set of distinct allele vectors, at most one will match Me patient vector. As before, we illustrate with the APOE genotype shown in Table 1

Table 1 illustrates. Consider a patient vector with a plaintext representation v=[1, 0]. Table B.1 below illustrates intermediate and match results. Since HE does not support logical operations, we use their arithmetic equivalents:

$XOR(a,b) = a+b-2ab,$ $OR(a,b) = a+b-ab.$

The advantage of using logical template matching over multiplication is that queries can be chained. There is no need for the client to interpret the results of the template match. The disadvantage of template matching is that the circuit depth is greater, and it depends upon the length of the variant vector.

| Template (t) | x = XOR(v, t) | h = 1 − OR(x) |
|---|---|---|
| [0, 1] | [1, 1] | 0 |
| [1, 1] | [0, 1] | 0 |
| [0, 0] | [1, 0] | 0 |
| [1, 0] | [0, 0] | 1 |

Table B.1 above illustrates template matching for APOE genotype. The template is shown in the left column, the intermediate result of the XOR operation is shown in the middle column. The match result is in the right column.

Summation Along a Vector

Summation of the elements of a vector is performed using shift and addition functions, which in some embodiments may be found in a library of homomorphic encryption functions. For a vector with n elements, $\lceil n \rceil$ shifts and additions may be required. Each shift is by $2^{(s-1)}$ elements, where s is the stage. Table C.1 below shows the operations on a plaintext vector of four elements. The final answer is given in the first element of the result vector. We multiply by a plaintext vector whose first element is one "1", and other elements are zero. This operation increases multiplicative depth by one.

| Stage | Initial | x0 | x1 | x2 | x3 | 0 |
|---|---|---|---|---|---|---|
| 1 | shift-1 | x1 | x2 | x3 | 0 | |
|   | add | x0 + x1 | x1 + x2 | x2 + x3 | x3 | |
| 2 | shift-2 | x2 + x3 | x3 | 0 | 0 | |
|   | add | x0 + x1 + x2 + x3 | x1 + x2 + x3 | x2 + x3 | x3 | |

Table C.1 illustrates the summation of values in a vector. Successive shift and add operations can be used to sum the elements of a vector. A four-element vector needs two stages. The first element of the result vector contains the sum (in bold font).

Testing and Results

CDS Applications

The method has been tested against three CDS applications: 1) clinical trial eligibility based on APOE haplotypes; 2) screening for familial hypercholesterolemia ("FH") based on LDLR pathogenic variants; and 3) interaction with clopidogrel based on CYP2C19 genotyping.

To test clinical trial eligibility, the query matrix encodes the question 'does the patient have at least one ε4 haplotype?'. The variants and haplotypes associated with this question are explained above. This query is of the form $<\hat{A}_4, \hat{v}>$ for each vector in the pair, where $A_4$ is the row-vector corresponding to the $\varepsilon_4$ haplotype.

To assess for FH and to differentiate between moderate and severe phenotypes, we can ask two queries: 1. How many pathogenic or likely pathogenic alleles are present in the LDLR gene? 2. How many homozygous pathogenic or likely pathogenic variants are present in the LDLR gene? The first query is a weighted summation of the form $<\hat{a}, \hat{v}_1+\hat{v}_2>$. The second query is a weighted summation $<\hat{a}, \hat{v}_1 \otimes \hat{v}_2>$. The vector a encodes pathogenic or likely pathogenic alleles, with a "1". If the answer to question 1 is zero, there is no evidence of FH. If the answer to question 1 is exactly one (i.e. only one gene affected), we predict a moderate phenotype. If the answer to question 2 is $>=1$ (i.e. both genes affected), we predict a severe phenotype. (For example, given. a=[0 . . . 1 1 0 . . . 1 0], if the patient had one homozygous pathogenic variant and a non-pathogenic variant, the vectors are $v_1$=[0 . . . 1 0 . . . 0] and $v_2$=[0 . . . 1 0 . . . 1], the answers would be 2 and 1 respectively, and the inference would be a severe risk of FH.) The phenotype is indeterminate (either moderate or severe) with other answers. For LDLR, we identified key variants. These were filtered to indels and single nucleotide variants ("SNVs") with pathogenic or likely pathogenic clinical status, review status of at least one star, and known start and end coordinates.

The phenotype for clopidogrel metabolism depends on the haplotypes of CYP2C19. We compute $\hat{h} = \hat{A} \hat{v}$ and return $\hat{h}$ to the client for decryption and argmax(h) to obtain haplotypes. The client applies a score to the haplotypes. The score maps to the phenotype: poor, intermediate, normal, rapid, ultra-rapid, or indeterminate metabolizer. We obtained variants, haplotype definitions, and genotype-phenotype mapping. An alternative solution that chains the genotype and phenotype queries is possible. In the chained method, the genotype is calculated by logical template matching and does not have to be decrypted by the client for the phenotype calculation.

Results

The operations for each application are given in Table 2 below. Measurements of time and memory consumption are given in Table 3 below. Timings were measured for key-generation, encryption, computation and decryption. The mean and standard deviation of these timings were computed over all the patients in the test set. We verified that the genotypes and phenotype results calculated over encryption matched ground-truth results generated with plaintext calculations and manual labeling of haplotypes.

| Application | Operations | Meaning |
|---|---|---|
| CYP2C19/Clopidogrel | $\hat{h}_1 = \hat{A} \hat{v}_1, \hat{h}_2 = \hat{A} \hat{v}_2$ | Haplotype match |
| LDLR/FH | $<\hat{a}, \hat{v}_1 + \hat{v}_2>$, $<\hat{a}, \hat{v}_1 \otimes \hat{v}_2>$ | Sum pathogenic mutations, Sum pathogenic homozygous variants |
| APOE/clinical trial | $<\hat{A}_4, \hat{v}_1>$, $<\hat{A}_4, \hat{v}_2>$ | Is the haplotype $\varepsilon_4$? |

Table 2 above illustrates the operations used for each application. The match in the first row of this table is the element of h that equals one.

The genome data and CDS query can be encrypted ahead of time in an offline, asynchronous manner. The query computation (shown by the "Query time" column) and the result decryption are real-time calculations, and the timings for these operations are more important for usability. Since the ciphertext vector length is fixed by the multiplication circuit-depth, the memory consumption or time do not increase with plaintext vector length, as long as the plaintext vector is smaller than the limit allowed by the ciphertext.

The presence of multiple ambiguous haplotypes does not change the timing or memory consumption because they are packed into the same ciphertext.

The table shows that the query time is different for the different applications. The CYP2C19 application requires as many dot-products as there are haplotypes. The APOE application requires only one dot-product because there is only one haplotype. The LDLR application requires an element-wise multiplication, followed by a dot-product, and an addition operation followed by a dot-product. The key generation depends on the multiplicative depth. The encryption of the operator depends on the operator. Each row of the matrix A is separately encrypted for CYP2C19, and therefore the encryption takes approximately 31 times as long as the encryption of the other operators. Since the vector length is fixed in all these applications, the encryption and decryption time is fixed.

| Application | Size of operator | Key generation | Encryption of operator | Encryption of vectors | Computation | Decryption | Memory (MB) |
|---|---|---|---|---|---|---|---|
| CYP2C19/ Clopidogrel | A = (31, 68) | 0.65/0.07 | 0.58/0.03 | 0.04/0.01 | 3.94/0.53 | 0.02/0.01 | 67 |
| LDLR/ FH | a = (1,2039) | 1.26/0.11 | 0.03/0.01 | 0.06/0.01 | 0.30/0.03 | 0.02/0.01 | 127 |
| APOE/ clinical trial | A_4 = (1,4) | 0.65/0.03 | 0.02/0.01 | 0.04/0.01 | 0.10/0.02 | 0.02/0.01 | 56 |

Table 3 illustrates time and memory consumption for the use-cases. Time (mean/std dev) was measured in seconds.

Accordingly, a new framework for secure computation on genomic data has been developed. The framework includes a vector representation for genomic data and a matrix or vector representation of CDS questions that can be applied as linear operations to the vectors. The representation allows HE and thus enables computation on a remote server with guarantees of security and privacy. The framework was validated with three CDS applications and 287 patients from the 1000-genomes dataset. Timing and memory measurements from the test-cases demonstrate the feasibility of using this approach. In this regard, query results (such as identified drug-gene interactions or positive genetic screening results), once computed, can be stored on servers where they can be accessed quickly for CDS.

A key component of the framework is the vector representation of the genome sequence, that allows queries on genome data to be expressed as mathematical operations. This representation is generalizable to a range of CDS applications as demonstrated by the three applications in the study that all used the same representation. As explained previously, each known variant is assigned a vector element. The scheme is extensible such that new variants of interest can be assigned to unoccupied elements of existing vectors or to new vectors. CDS queries are performed as mathematical operations, unlike other CDS systems that commonly use Boolean logical operations. To make it easier for CDS systems to query the secure GACS, common patterns of queries may be encapsulated into functions that automatically generate the query matrices. In this way, the system provides a computationally efficient and secure way to process and store genomic data.

Each communication interface described herein generally includes hardware, and, in some instances, software, that enables the computer system, to transport, send, receive, and/or otherwise communicate information to and/or from the communication interface of one or more other systems on the network. For example, the communication interface of the user input system may include a wireless transceiver, modem, server, electrical connection, and/or other electronic device that operatively connects the user input system to another system. The wireless transceiver may include a radio circuit to enable wireless transmission and reception of information.

As will be appreciated by one of ordinary skill in the art, the present invention may be embodied as an apparatus (including, for example, a system, a machine, a device, a computer program product, and/or the like), as a method (including, for example, a business process, a computer-implemented process, and/or the like), or as any combination of the foregoing. Accordingly, embodiments of the present invention may take the form of an entirely software embodiment (including firmware, resident software, microcode, and the like), an entirely hardware embodiment, or an embodiment combining software and hardware aspects that may generally be referred to herein as a "system." Furthermore, embodiments of the present invention may take the form of a computer program product that includes a computer-readable storage medium having computer-executable program code portions stored therein.

As the phrase is used herein, a processor may be "configured to" perform a certain function in a variety of ways, including, for example, by having one or more general-purpose circuits perform the function by executing particular computer-executable program code embodied in computer-readable medium, and/or by having one or more application-specific circuits perform the function.

It will be understood that any suitable computer-readable medium may be utilized. The computer-readable medium may include, but is not limited to, a non-transitory computer-readable medium, such as a tangible electronic, magnetic, optical, infrared, electromagnetic, and/or semiconductor system, apparatus, and/or device. For example, in some embodiments, the non-transitory computer-readable medium includes a tangible medium such as a portable computer diskette, a hard disk, a random access memory (RAM), a read-only memory (ROM), an erasable programmable read-only memory (EEPROM or Flash memory), a compact disc read-only memory (CD-ROM), and/or some other tangible optical and/or magnetic storage device. In other embodiments of the present invention, however, the computer-readable medium may be transitory, such as a propagation signal including computer-executable program code portions embodied therein.

It will also be understood that one or more computer-executable program code portions for carrying out the specialized operations of the present invention may be required on the specialized computer include object-oriented, scripted, and/or unscripted programming languages, such as, for example, Java, Perl, Smalltalk, C++, SAS, SQL, Python, Objective C, and/or the like. In some embodiments, the one or more computer-executable program code portions for carrying out operations of embodiments of the present invention are written in conventional procedural programming languages, such as the "C" programming languages and/or similar programming languages. The computer program code may alternatively or additionally be written in one or more multi-paradigm programming languages, such as, for example, F #.

Embodiments of the present invention are described above with reference to flowcharts and/or block diagrams. It will be understood that steps of the processes described herein may be performed in orders different than those illustrated in the flowcharts. In other words, the processes represented by the blocks of a flowchart may, in some embodiments, be in performed in an order other that the order illustrated, may be combined or divided, or may be performed simultaneously. It will also be understood that the blocks of the block diagrams illustrated, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

It will also be understood that the one or more computer-executable program code portions may be stored in a transitory or non-transitory computer-readable medium (e.g., a memory, and the like) that can direct a computer and/or other programmable data processing apparatus to function in a particular manner, such that the computer-executable program code portions stored in the computer-readable medium produce an article of manufacture, including instruction mechanisms which implement the steps and/or functions specified in the flowchart(s) and/or block diagram block(s).

The one or more computer-executable program code portions may also be loaded onto a computer and/or other programmable data processing apparatus to cause a series of operational steps to be performed on the computer and/or other programmable apparatus. In some embodiments, this produces a computer-implemented process such that the one or more computer-executable program code portions which execute on the computer and/or other programmable apparatus provide operational steps to implement the steps specified in the flowchart(s) and/or the functions specified in the block diagram block(s). Alternatively, computer-implemented steps may be combined with operator and/or human-implemented steps in order to carry out an embodiment of the present invention.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. A computer-implemented method for encoding genomics data for secure storage and processing, the computer-implemented method comprising:
   receiving a set of genomic data;
   receiving a set of genomic queries;
   encoding, using an encoding algorithm, the set of genomic data to produce an encoded set of genomic data; and
   encoding, using the encoding algorithm, the set of genomic queries to produce an encoded set of genomic queries, wherein the encoding algorithm comprises at least one of a phased encoding scheme or an unphased encoding scheme, wherein executing the encoding algorithm comprises:
      generating one or more vectors for one or more key variants associated with the set of genomic data; and
      generating, based on the set of genomic queries, one or more computations on the one or more vectors.

2. The computer-implemented method according to claim 1, wherein the computer-implemented method further comprises:
   encrypting, using an encryption algorithm, the encoded set of genomics data to produce an encrypted set of genomic data;
   encrypting, using the encryption algorithm, the encoded set of genomic queries to produce an encrypted set of genomic queries; and
   transmitting the encrypted set of genomic data and the encrypted set of genomic queries to a genomic data processing computing device.

3. The computer-implemented method according to claim 2, wherein the encryption algorithm is a homomorphic encryption algorithm.

4. The computer-implemented method according to claim 2, wherein the computer-implemented method further comprises:
   receiving an output from the genomic data processing computing device, wherein the output comprises an analysis of the encrypted set of genomic data based on the encrypted set of genomic queries, wherein the output is encrypted using the encryption algorithm; and
   decrypting the output using a private key associated the encryption algorithm.

5. A system for encoding genomics data for secure storage and processing, the system comprising:
   a memory device with computer-readable program code stored thereon;
   a communication device; and
   a processing device operatively coupled to the memory device and the communication device, wherein the processing device is configured to execute the computer-readable program code to:
   receive a set of genomic data;
   receive a set of genomic queries;
   encode, using an encoding algorithm, the set of genomic data to produce an encoded set of genomic data; and
   encode, using the encoding algorithm, the set of genomic queries to produce an encoded set of genomic queries, wherein the encoding algorithm comprises at least one of a phased encoding scheme or an unphased encoding scheme, wherein executing the encoding algorithm comprises:

generating one or more vectors for one or more key variants associated with the set of genomic data; and generating, based on the set of genomic queries, one or more computations on the one or more vectors.

6. The system according to claim 5, wherein the computer-readable program code, when executed, further causes the processing device to:

encrypt, using an encryption algorithm, the encoded set of genomics data to produce an encrypted set of genomic data;

encrypt, using the encryption algorithm, the encoded set of genomic queries to produce an encrypted set of genomic queries; and transmit the encrypted set of genomic data and the encrypted set of genomic queries to a genomic data processing computing device.

7. The system according to claim 6, wherein the encryption algorithm is a homomorphic encryption algorithm.

8. The system according to claim 6, wherein the computer-readable program code, when executed, further causes the processing device to:

receive an output from the genomic data processing computing device, wherein the output comprises an analysis of the encrypted set of genomic data based on the encrypted set of genomic queries, wherein the output is encrypted using the encryption algorithm; and decrypt the output using a private key associated with the encryption algorithm.

9. A computer program product for encoding genomics data for secure storage and processing, the computer program product comprising at least one non-transitory computer readable medium having computer-readable program code portions embodied therein, the computer-readable program code portions comprising executable code portions for:

receiving a set of genomic data;

receiving a set of genomic queries;

encoding, using an encoding algorithm, the set of genomic data to produce an encoded set of genomic data; and encoding, using the encoding algorithm, the set of genomic queries to produce an encoded set of genomic queries, wherein the encoding algorithm comprises at least one of a phased encoding scheme or an unphased encoding scheme, wherein executing the encoding algorithm comprises:

generating one or more vectors for one or more key variants associated with the set of genomic data; and generating, based on the set of genomic queries, one or more computations on the one or more vectors.

10. The computer program product according to claim 9, wherein the computer-readable program code portions further comprise executable portions for:

encrypting, using an encryption algorithm, the encoded set of genomics data to produce an encrypted set of genomic data;

encrypting, using the encryption algorithm, the encoded set of genomic queries to produce an encrypted set of genomic queries; and transmitting the encrypted set of genomic data and the encrypted set of genomic queries to a genomic data processing computing device.

11. The computer program product according to claim 10, wherein the encryption algorithm is a homomorphic encryption algorithm.

12. The computer program product according to claim 10, wherein the computer-readable program code portions further comprise executable portions for:

receiving an output from the genomic data processing computing device, wherein the output comprises an analysis of the encrypted set of genomic data based on the encrypted set of genomic queries, wherein the output is encrypted using the encryption algorithm; and decrypting the output using a private key associated the encryption algorithm.

* * * * *